United States Patent [19]

Mulder et al.

[11] Patent Number: 5,148,465
[45] Date of Patent: Sep. 15, 1992

[54] X-RAY EXAMINATION APPARATUS AND FILTER SUITABLE FOR USE THEREIN

[75] Inventors: Jakob W. Mulder, Eindhoven, Netherlands; Goedele A. M. Sibbens, Turnhout, Belgium

[73] Assignee: U.S. Philips Corporation, New York, N.Y.

[21] Appl. No.: 682,807

[22] Filed: Apr. 8, 1991

[30] Foreign Application Priority Data

Apr. 17, 1990 [NL] Netherlands ............... 9000896

[51] Int. Cl.$^5$ .................................. G21K 1/10
[52] U.S. Cl. ................................ 378/156; 378/159
[58] Field of Search ............ 378/145, 156, 158, 159, 378/62

[56] References Cited

U.S. PATENT DOCUMENTS

| 3,755,672 | 8/1973 | Edholm et al. | 378/158 |
| 4,101,766 | 7/1978 | Minami et al. | 378/159 |
| 4,300,055 | 11/1981 | Taumann | 378/159 |
| 4,481,419 | 11/1984 | Persyk | 378/159 |

FOREIGN PATENT DOCUMENTS

| 689868 | 4/1940 | Fed. Rep. of Germany. | |
| 0086095 | 6/1980 | Japan | 378/159 |

Primary Examiner—David P. Porta

[57] ABSTRACT

A lens-like X-ray filter is filled with a liquid, the filter having flexible walls, the filter being between an X-ray source and an X-ray detector in an X-ray examination apparatus. The filter obviates brightness variations in an X-ray image caused by vignetting. The filter thickness is adjustable by the supply and the discharge of a liquid, the filter preserving a quadratic thickness variation from the center to the edges.

17 Claims, 1 Drawing Sheet

X-RAY EXAMINATION APPARATUS AND FILTER SUITABLE FOR USE THEREIN

FIELD OF THE INVENTION

The invention relates to an X-ray examination apparatus comprising an X-ray source and a detector for detecting X-rays to be transmitted by the X-ray source for forming an X-ray image, an X-ray absorbing filter being arranged between the X-ray source and the X-ray detector, which includes a liquid reservoir placeable in the X-ray beam and having a first and a second wall, the first wall being flexible.

The invention also relates to a filter suitable for use in such an X-ray examination apparatus.

BACKGROUND OF THE INVENTION

Such an X-ray examination apparatus and filter are disclosed in DE 689 868. In this Patent Specification a filter is described for use in a medical X-ray examination apparatus, the filter being formed by a liquid space between two flexible walls. The filter is arranged between an X-ray source and an X-ray detector. An X-ray absorbing liquid can be inserted between the walls. The walls have such a curvature, that X-ray radiation received from an X-ray focus is spatially uniformly attenuated by the filter. The path length of X-rays passing through the filter at its edges, is equal to the path length of X-rays passing through the center portion of the filter. The filter has for its object to remove the low-energetic X-ray radiation, which contributes only little to the image being formed, from the beam. This reduces the dose of radiation to which a patient is exposed during a medical examination.

In X-ray examination apparatuses in which an X-ray image is displayed as a televison picture on a monitor with the aid of an X-ray image intensifier tube and a television pick-up device coupled thereto, vignetting occurs due to the geometry of an input screen of the X-ray image intensifier tube and the presence, if any, of optical means between the television pick-up device and the X-ray image intensifier tube. As a result thereof, the edges of the X-ray image become darker than center portions of the X-ray image, even in the case of an uniform irradiation of the X-ray image intensifier tube. The invention has inter alia for its object to provide an X-ray absorbing filter, which reduces the spatial brightness variation in an X-ray image, produced by vignetting.

SUMMARY OF THE INVENTION

Therefore, according to the invention, an X-ray examination apparatus, comprises a liquid reservoir which has a wall spacing which decreases from the reservoir center to the edges in order to reduce vignetting when the detector is irradiated by a uniform X-ray beam.

The liquid pressure causes the flexible wall to become curved, with a maximum deviation relative to the second wall in the center portion of the filter. The brightness variation of the X-ray image due to vignetting shows in a first approximation a quadratic decrease from the center of the X-ray image towards the edges. When a filter thickness is used which is small with respect to an attenuation length of the X-ray radiation on attenuation by the filter fluid, the attenuation increases approximately linearly with filter thickness and the spatial brightness variation due to vignetting is compensated for by the filter.

A preferred embodiment of an X-ray examination apparatus in accordance with the invention, is one where, the second wall of the filter is a rigid wall.

A rigid wall can, for example, be fitted to an exterior side of the X-ray source and permits the filter can be handled with greater ease on, for example, exchange of the filter. A material for the rigid wall can be chosen such, that a desired filtration of the X-ray spectrum is effected. A proper seal between the flexible wall and the rigid wall can be obtained by using an anular clamping member.

An embodiment of an X-ray examination apparatus in accordance with the invention, in which the second wall of the filter is flexible, comprises one where, the second wall has a curvature opposite to the curvature of the first wall.

Two flexible walls which have their edges sealed together in a fluid-tight manner, for example by clamping them between two anular clamping members, assume a paraboloid shape, the walls curving in opposite directions. For small filter thicknesses for which the exponential attenuation varies approximately linearly versus the filter thickness, the attenuation is twice as high when two flexible walls are used than when one flexible wall is utilized. Consequently, a higher attenuation can be obtained at a smaller stretch of the flexible walls, so that the paraboloid shape of the filter is maintained to an improved extent.

A further preferred embodiment of an X-ray examination apparatus in accordance with the invention, comprises a filter connected to a fluid pump.

Via a pump which is controlled, for example, in dependence on a video signal from the television pick-up device, a filter thickness setting can be effected by the supply and discharge of fluid to and from the reservoir. The filter is adjusted such, that on irradiation of the X-ray detector by a uniform X-ray beam, the video signal from the picture edges of the X-ray image is approximately equal to the video signal from the centre portions of the X-ray image. Such a setting is necessary since the vignetting changes when the spacing between the X-ray source and the X-ray detector is varied.

BRIEF DESCRIPTION OF THE DRAWING

Some embodiments of a filter in accordance with the invention will now be described in greater detail with reference to the accompanying drawing. In the drawing.

DETAILED DESCRIPTION OF THE PREFERRED EMBODIMENT

Figure 1:
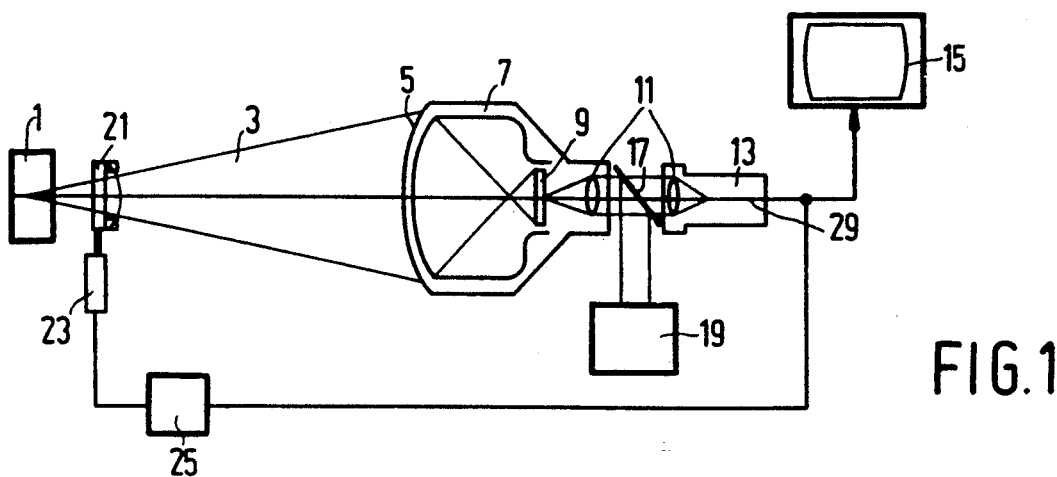
FIG. 1 shows an X-ray examination apparatus according to an embodiment of the invention.

FIG. 1 shows an X-ray examination apparatus including an X-ray source 1 for transmitting a beam of X-rays 3. The beam of X-rays 3 impinges upon an input screen 5 of an X-ray image intensifier tube 7. The input screen 5 has a phosphor layer located behind a glass or aluminium envelope and in which the X-ray beam 3 effects luminescence. With the aid of a photocathode the light quanta emitted by the phosphor are captured and electrons are released which are accelerated to, for example, 20 keV and are displayed on an output screen 9. Via a twin optical system 11 the luminous image from the output screen is displayed on an input screen of a television pick-up device 13. A partially transmitting mirror 17 which projects the luminous image originating from the output screen onto a photographic film in a film camera 19 is between the lenses of the twin optical system 11. The television pick-up device 13 generates a video signal which is proportional to the light intensity detected at its input screen. The video signal is applied to a television monitor 15 and to a control device 25. Arranged between the X-ray source 1 and the X-ray image intensifier tube 7 is an adjustable filter 21 which via a fluid pump 23 is adjustable by the control device 25 in dependence on the video signal. Then, fluid is supplied to or withdrawn from the filter by the pump 23 until on uniform irradiation of the input screen 5 the video signal for edges of an X-ray image is equal to the video signal for center portions of the X-ray image.

Figure 2:
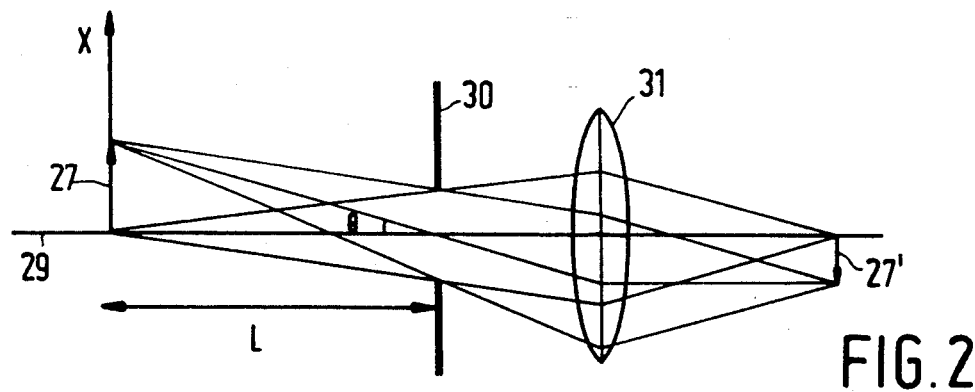
FIG. 2 is a schematic representation of vignetting by a bounding aperture on display through a lens.

FIG. 2 shows schematically how an object 27 extending in an x-direction located transversely of the optical axis 29 is displayed by a lens 31. An apertured diaphragm 30 is between the object 27 and the lens 31. When the object 27 is a uniform line source, then the flux passing through the aperture of the diaphragm 30 varies proportionally to $(\cos\theta)^4$, wherin $\theta$ is the angle of the radius between the portion of the object emitting the flux and the center of the aperture to the optical axis 29. For Gaussian systems, in which a distance in the x-direction is small compared to the dimensions of the system along the optical axis 29, the following approximation can be made for an object located at a distance L from the diaphragm 30:

$$(\cos\theta)^4 \simeq 1 - 2\theta^2 \simeq 1 - \frac{2x^2}{L^2}$$

An image 27' of the object 27 has, because of the bounding diaphragm 30 an intensity variation which quadratically decreases relative to the optical axis 29. For a length L of 5 cms. and a distance x to the optical axis of 1 cm this approximation is accurate to within 0.5%.

Figure 3:
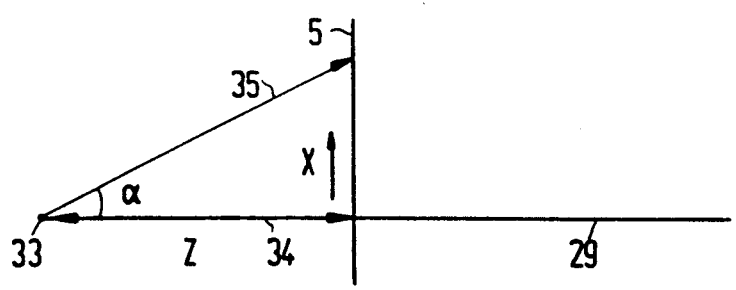
FIG. 3 shows schematically intensity variations due to the input screen geometry of an X-ray image intensifier tube.

FIG. 3 shows how a beam of X-rays impinging from the X-ray focus 33 onto the input screen 5 of the X-ray image intensifier tube has on the input screen a higher intensity than an X-ray beam 35 incident on the input screen 5 at an angle $\alpha$ relative to the optical axis. The intensity on the input screen varies as $(\cos\alpha)^3$, which for small distances of x with respect to Z can be approximated by:

$$(\cos\alpha)^3 \simeq \left(1 - \frac{\alpha^2}{2}\right)^3 \simeq \left(1 - \frac{3x^2}{2Z^2}\right)$$

Herein Z is the spacing between the X-ray focus 33 and the input screen 5. For a value of 1 meter for Z this approximation is accurate to within 0.02%.

Both vignetting due to bounding apertures in the optical system of the X-ray imaging system and the decrease in intensity due to the geometry of the input screen of the X-ray image intensifier tube can be compensated for by the filter 21 between the X-ray source 1 and the X-ray image intensifier tube 7. For water, an attenuation length amounts to approximately 3 cm. for X-rays generated in an X-ray tube at approximately 80 kV. For a maximum filter thickness of 0.5 cm (in the center of the filter) the attenuation is linear within a margin of 0.5%. A layer of water having a thickness which decreases quadratically, provided between the source 1 and the X-ray image intensifier tube 7 can compensate for vignetting. Since vignetting varies versus the distance Z between the X-ray source 1 and the X-ray image intensifier tube 7, it is advantageous for the filter thickness to be variable.

Figure 4:
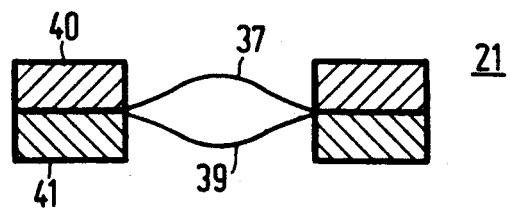
FIG. 4 is a cross-sectional view of a filter of the invention.

FIG. 4 shows a filter 21, two flexible X-ray radiation transparent walls 37 and 39 being clamped between two anular clamping members 40 and 41. The walls 37 and 39 may be rubber or thermoplastic, for example.

Figure 5:
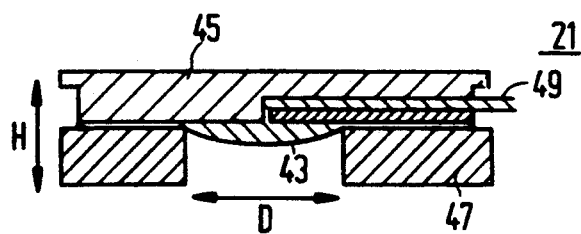
FIG. 5 is a cross-sectional view of a filter in accordance with the invention.

FIG. 5 shows an X-ray radiation transparent filter 21, a flexible wall 43 being clamped between a rigid wall 45 of, for example, Perspex, an X-ray transparent thermoplastic material, and an anular clamping member 47. In this situation the filter has, for example, a diameter D of 10 cm. and a maximum height H of 2.5 cm. The filter is connected to the fluid pump 23, not shown, via a supply line 49. For an adequate form-retaining capacity of the flexible wall 43, not disturbed by force of gravity effects, the overpressure in the filter preferably exceeds 0.5 atmosphere.

The walls curve in a lens-like arrangement in which the central region has the greatest spacing between the filter walls and the spacing decreases to the wall edges in a curve-like manner to a minimum similar to an optical lens.

What is claimed is:

1. An X-ray examination apparatus comprising an X-ray source and a detector for detecting a beam of X-rays transmitted by the X-ray source for forming an X-ray image, an X-ray absorbing filter between the X-ray source and the X-ray detector, said filter including a liquid reservoir adapted for placement in the X-ray beam and having a first and second wall, at least the first wall being flexible, said first and second walls for receiving said liquid reservoir therebetween and having a wall spacing which decreases from the reservoir center to the reservoir edges, said wall spacing being dimensioned to reduce vignetting in response to irradiation of the detector by a uniform X-ray beam.

2. An X-ray examination apparatus as claimed in claim 1, wherein the second wall is rigid.

3. An X-ray examination apparatus as claimed in claim 2, the first wall of the filter is connected at said edges to the second wall via an anular clamping member.

4. An X-ray examination apparatus as claimed in claim 1 wherein both walls of the filter are flexible, the first wall has a curvature opposite to the curvature of the second wall.

5. An X-ray examination apparatus as claimed in claim 4, wherein the walls of the filter are clamped between two anular clamping members in a liquid-tight manner.

6. An X-ray examination apparatus as claimed in claim 1 including a pump connected to the filter.

7. An X-ray examination apparatus as claimed in claim 5 including a pump connected to the filter.

8. A filter for use with an X-ray examination apparatus comprising an X-ray source and an X-ray detector for detecting a beam of X-rays transmitted by the X-ray source for forming an image, said image exhibiting vignetting, said filter comprising:

a first wall;

a second wall, at least one of said walls being flexible; and means for securing the filter in said beam and the walls to each other at their edges to form a liquid receiving cavity therebetween, said walls being so spaced and so dimensioned such that said cavity has a spacing which decreases from the cavity central region towards said edges in a manner to reduce said vignetting.

9. The filter of claim 8 wherein the at least one wall curves from said central region towards said edges.

10. The filter of claim 8 wherein both walls are flexible.

11. The filter of claim 8 further including pump means coupled to said cavity for pumping liquid to and from said cavity for adjusting the spacing of said walls.

12. The filter of claim 10 wherein the walls are mirror images of each other curving from the central region to their edges.

13. The filter of claim 8 including filter adjust means coupled to said cavity for adjusting the spacing of said walls and thus the size of said cavity to thereby adjust the amount of vignetting that is reduced.

14. The filter of claim 13 wherein the filter adjust means includes means for adjusting the pressure of said liquid in said cavity to thereby flex said at least one wall.

15. The filter of claim 8 wherein the spacing between the walls at said central region decreases to the spacing of the walls at said edges according to a quadratic relationship.

16. An X-ray examination apparatus comprising an X-ray source and a detector for detecting a beam of X-rays transmitted by the X-ray source for forming an X-ray image, an X-ray absorbing filter between the X-ray source and the X-ray detector, said filter including a liquid reservoir adapted for placement in the X-ray beam and having a first and second wall, at least the first wall being flexible, said first and second walls for receiving said liquid reservoir therebetween and having a wall spacing which decreases from the reservoir center to the reservoir edges to reduce vignetting in response to irradiation of the detector by a uniform X-ray beam, both walls of the filter being flexible, the first wall having a curvature opposite to the curvature of the second wall.

17. A filter for use with an X-ray examination apparatus comprising an X-ray source and an X-ray detector for detecting a beam of X-rays transmitted by the X-ray source for forming an image, said image exhibiting vignetting, said filter comprising:

a first wall;

a second wall, at least one of said walls being flexible; and means for securing the filter in said beam and the walls to each other at their edges to form a liquid receiving cavity therebetween, said walls being spaced so that said cavity has a spacing which decreases from the cavity central region towards said edges in a manner to reduce said vignetting, both said walls being flexible.

* * * * *